US012178859B2

(12) United States Patent
Kageshima et al.

(10) Patent No.: US 12,178,859 B2
(45) Date of Patent: Dec. 31, 2024

(54) ANTI INFLAMMATORY COMPOSITION

(71) Applicants: WAKO FILTER TECHNOLOGY CO., LTD., Tokyo (JP); TEIKYO UNIVERSITY, Tokyo (JP)

(72) Inventors: Hiroki Kageshima, Nagareyama (JP); Yoichi Murakami, Koga (JP); Akira Saito, Tokyo (JP); Shigeru Abe, Hachioji (JP); Kazumi Hayama, Hachioji (JP); Naho Maruyama, Hachioji (JP)

(73) Assignees: WAKO FILTER TECHNOLOGY CO., LTD., Tokyo (JP); TEIKYO UNIVERSITY, Tokyo (JP)

( * ) Notice: Subject to any disclaimer, the term of this patent is extended or adjusted under 35 U.S.C. 154(b) by 701 days.

(21) Appl. No.: 17/423,066

(22) PCT Filed: Jan. 14, 2020

(86) PCT No.: PCT/JP2020/000892
§ 371 (c)(1),
(2) Date: Jul. 14, 2021

(87) PCT Pub. No.: WO2020/149263
PCT Pub. Date: Jul. 23, 2020

(65) Prior Publication Data
US 2022/0072109 A1 Mar. 10, 2022

(30) Foreign Application Priority Data
Jan. 15, 2019 (JP) .................. 2019-004641

(51) Int. Cl.
*A61K 38/47* (2006.01)
*A61K 47/61* (2017.01)
*A61P 29/00* (2006.01)

(52) U.S. Cl.
CPC .............. *A61K 38/47* (2013.01); *A61K 47/61* (2017.08); *A61P 29/00* (2018.01); *C12Y 302/01017* (2013.01)

(58) Field of Classification Search
CPC ...... A61K 38/47; A61K 47/61; A61K 31/045; A61K 31/122; A61K 31/19; A61K 31/20; A61P 29/00; A61P 17/00; A61P 43/00; C12Y 302/01017
See application file for complete search history.

(56) References Cited

U.S. PATENT DOCUMENTS

| 10,729,779 | B2* | 8/2020 | Kageshima .... C12Y 302/01017 |
| 11,344,625 | B2* | 5/2022 | Kageshima .......... A61K 31/045 |
| 2019/0022238 | A1* | 1/2019 | Kageshima ............ A61K 31/10 |
| 2019/0053489 | A1 | 2/2019 | Miyazaki et al. |
| 2019/0360528 | A1 | 11/2019 | Kouno et al. |
| 2020/0360528 | A1 | 11/2020 | Kageshima et al. |

FOREIGN PATENT DOCUMENTS

| CN | 108025043 A * | 5/2018 | .......... A61K 31/045 |
| JP | 2017/226615 | 12/2017 | |
| WO | WO 2017/038872 | 3/2017 | |
| WO | WO-2017038872 A1 * | 3/2017 | .......... A61K 31/045 |
| WO | WO 2017/138476 | 8/2017 | |

OTHER PUBLICATIONS

Desai JV, Lionakis MS. The role of neutrophils in host defense against invasive fungal infections. Curr Clin Microbiol Rep. Sep. 2018;5(3):181-189. doi: 10.1007/s40588-018-0098-6. Epub Jun. 22, 2018. PMID: 31552161; PMCID: PMC6758935. (Year: 2018).*
CN108025043A. Derwnet english translation (12 pages) (Year: 2018).*
Chung et al., *Suppressive effects of lysozyme on polyphosphate-mediated vascular inflammatory responses*, 474 Biochemical and Biophysical Research Communications 715-721 (2016).
Maruyama et al., *The anti-fungal and anti-inflammatory effects of essential oils—the possibility for treatment on superficial mycoses*, 43(3) Journal of Japan Association of Odor Environment 199-210 (2012).
Nagaoka et al., *Inhibitory actions of glucosamine on neutrophil functions*, 22(5) Inflammation and Regeneration 461-468 (Sep. 2002).
Ohota et al., *Priming of neutrophil respiratory burst by tumor necrosis factor-α*, 35(4) The Society of Analytical Bio-Science 322-328 (2012).
Wardani et al., *Immunostimulatory Activity of Chitosan Nanoparticles on Wistar Albino Rats*, 10(5) Pharmacognosy Journal 892-898 (Abstract) (2018).

* cited by examiner

*Primary Examiner* — Aaron J Kosar
(74) *Attorney, Agent, or Firm* — Panitch Schwarze Belisario & Nadel LLP; Erin M. Dunston

(57) ABSTRACT

The present invention provides a method for treating or preventing inflammation caused by neutrophils and a pharmaceutical composition for such treatment or prevention. Specifically, provided is a pharmaceutical composition or the like for treating or preventing inflammation caused by neutrophils that contains a complex in which lysozyme and chitosan are bonded.

12 Claims, 5 Drawing Sheets

LYSOZYME-CHITOSAN COMPLEX

DECANOIC ACID (a) CONTROL
(FREE OF LYSOZYME-CHITOSAN COMPLEX AND DECANOIC ACID)

(b) LYSOZYME-CHITOSAN COMPLEX: 0.2 mg/ml (0.02%)
 +DECANOIC ACID: 0.4 mg/ml (0.04%)

(c) LYSOZYME-CHITOSAN COMPLEX: 0.2 mg/ml (0.02%)

(d) DECANOIC ACID: 0.4 mg/ml (0.04%)

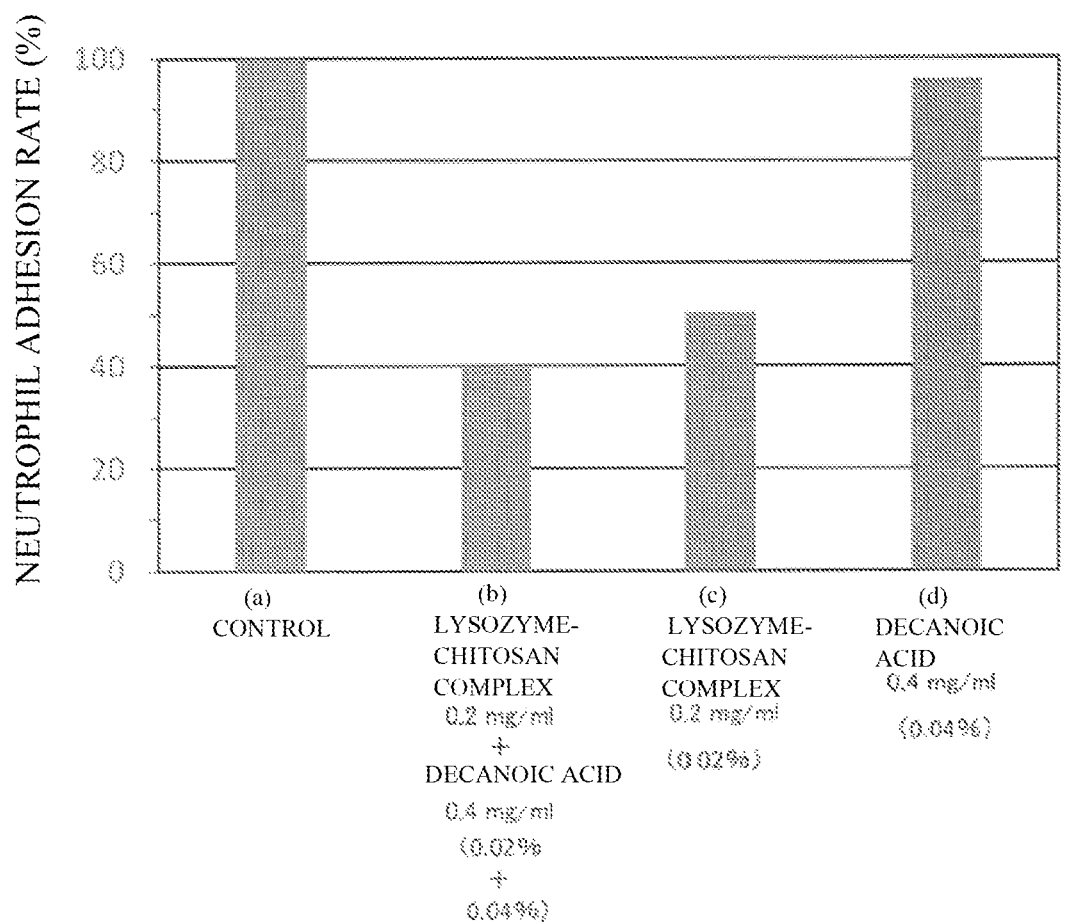

ANTI INFLAMMATORY COMPOSITION

CROSS-REFERENCE TO RELATED APPLICATIONS

This application is a U.S. National Stage Application pursuant to 35 U.S.C. § 371 of International Patent Application PCT/JP2020/000892, filed on Jan. 14, 2020, and published as WO 2020/0149263 on Jul. 23, 2020, which claims priority to Japanese Patent Application 2019-004641, filed on Jan. 15, 2021, all of which are incorporated herein by reference in their entireties for all purposes.

TECHNICAL FIELD

The present invention relates to a composition capable of treating or preventing neutrophil-induced inflammation, and more specifically to a pharmaceutical composition for treating or preventing neutrophil-induced inflammation, which contains a complex of lysozyme and chitosan bound together.

BACKGROUND ART

Neutrophils are a type of polymorphonuclear leukocyte found in the blood, and migrate from blood vessels into tissues toward the site of inflammation. The neutrophils having migrated from blood vessels to the site of inflammation feed on foreign substances. In addition, neutrophils are activated to produce reactive oxygen species (such as hydrogen peroxide and hydroxyl radicals) and release them into the extracellular space, and release granule components such as proteolytic enzymes into the extracellular space. These reactive oxygen species and granule components have a strong cytotoxic effect and have the ability to suppress inflammatory reactions. On the other hand, it is known that the production of excessive reactive oxygen species by activated neutrophils accumulated at the site of inflammation causes damaging effects (adverse effects) to cellular tissues other than the site of inflammation (Non-Patent Literatures 1 to 3). Targeting the damaging effects caused by neutrophils, it has been considered to use glucosamine and plant essential oils in order to suppress the excessive activation of neutrophils (Non-Patent Literatures 2 and 3). However, the relationship between the complex of lysozyme and chitosan bound together and neutrophils has not been investigated so far.

CITATION LIST

Patent Literatures

Patent Literature 1: International Publication No. WO2017/038872 Pamphlet
Patent Literature 2: International Publication No. WO2017/138476 Pamphlet
Patent Literature 3: Japanese Patent Application Publication No. 2017-226615

Non-Patent Literatures

Non-Patent Literature 1: Yasuhiko Ohota et al., "Priming of neutrophil respiratory burst by tumor necrosis factor-α," the Society of Analytical Bio-Science Vol. 35, No. 4, 2012, pp. 322 to 328
Non-Patent Literature 2: Isao Nagaoka et al., "Inhibitory actions of glucosamine on neutrophil functions," Inflammation and Regeneration Vol. 22, No. 5, September 2002, pp. 461 to 468
Non-Patent Literature 3: Naho Maruyama and Shigeru Abe, "Antifungal and anti-inflammatory effects of plant essential oils—Potential for the treatment of fungal infections-" J. Japan Association on Odor Environment, Vol. 43, No. 3, 2012, pp. 199 to 210

SUMMARY OF INVENTION

An object of the present invention is to provide a pharmaceutical composition, a therapeutic agent, and a preventive agent for treating or preventing neutrophil-induced inflammation, as well as a method for producing the same.

Another object of the present invention is to use a pharmaceutical composition containing a complex of lysozyme and chitosan bound together to treat or prevent neutrophil-induced inflammation.

The inventors of the present invention have made earnest studies on the relationship between a complex of lysozyme and chitosan bound together and neutrophils, and have found as a result that the complex of lysozyme and chitosan bound together can suppress the adhesive reaction of neutrophils at the site of inflammation. As a result, it has been concluded that regarding the inflammatory reaction caused by excessive activation of neutrophils and excessive production of reactive oxygen species at the site of inflammation, the inflammatory reaction can be suppressed by applying a complex of lysozyme and chitosan bound together to the site of inflammation. Thus, the present invention has been completed. Specifically, the present invention may have the following aspects.

[1] A pharmaceutical composition for treating or preventing neutrophil-induced inflammation, including: a complex of lysozyme and chitosan bound together.

[2] The pharmaceutical composition according to [1] described above, wherein the chitosan is a water-soluble chitosan having a molecular weight of 1000 Da to 30,000 Da.

[3] The pharmaceutical composition according to [1] or [2] described above, wherein the complex is contained at 0.01 mg/ml to 50 mg/ml in the pharmaceutical composition.

[4] The pharmaceutical composition according to any one of [1] to [3] described above, wherein the complex is contained at 0.001% by mass to 5.0% by mass in the pharmaceutical composition.

[5] The pharmaceutical composition according to any one of [1] to [4] described above, further including a terpene alcohol, a fatty acid, and/or a salt of the fatty acid.

[6] The pharmaceutical composition according to any one of [1] to [4] described above, further including a fatty acid having 8 to 12 carbon atoms or a salt of the fatty acid.

[7] The pharmaceutical composition according to [6] described above, wherein the fatty acid is decanoic acid or lauric acid.

[8] The pharmaceutical composition according to any one of [1] to [7] described above, further including a terpene alcohol, wherein the terpene alcohol is terpinen-4-ol, hinokitiol, or geraniol.

[9] The pharmaceutical composition according to any one of [1] to [8] described above, wherein the neutrophil-induced inflammation is dermatitis or pyoderma.

[10] Use of a complex of lysozyme and chitosan bound together in production of a pharmaceutical composition for treating or preventing neutrophil-induced inflammation.

Advantageous Effects of Invention

The present invention makes it possible to provide a pharmaceutical composition, a therapeutic agent, and a preventive agent for treating or preventing neutrophil-induced inflammation, as well as a method for producing the same.

Also, it is possible to use a pharmaceutical composition containing a complex of lysozyme and chitosan bound together to treat or prevent neutrophil-induced inflammation.

BRIEF DESCRIPTION OF DRAWINGS

FIG. 4 is a graph showing neutrophil adhesion rates (%) in the case of using various test substances.

DESCRIPTION OF EMBODIMENTS

<Pharmaceutical Composition>

The present invention relates to a pharmaceutical composition for treating or preventing neutrophil-induced inflammation, which contains a complex of lysozyme and chitosan bound together. Hereinafter, the present invention is specifically described.

Figure 1:
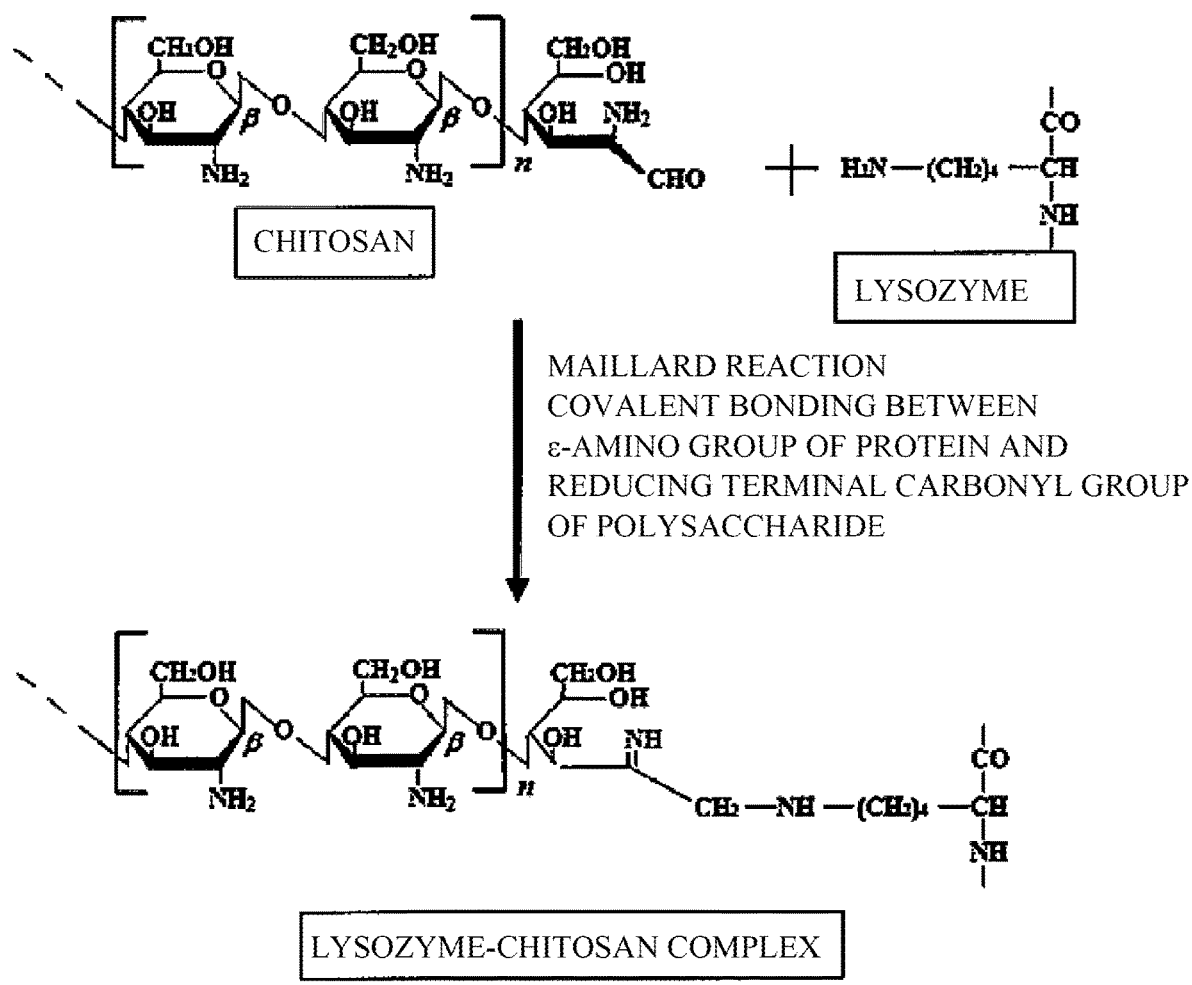
FIG. 1 is a schematic diagram of a reaction when synthesizing a complex of lysozyme and chitosan bound together.

The "complex of lysozyme and chitosan bound together" is a complex in which lysozyme and chitosan are bound by, for example, the Maillard reaction (see FIG. 1). Lysozyme and water-soluble chitosan bound by the Maillard reaction mask most or all of the antigenic structures in lysozyme, making the lysozyme-chitosan complex less likely to cause allergies even when ingested by humans. Alternatively, a cross-linking agent can be used to covalently bond lysozyme and chitosan to obtain the above complex.

Here, "lysozyme" is an enzyme that hydrolyzes mucopolysaccharides, and chicken-derived lysozyme and human-derived lysozyme can be preferably used.

"Chitosan" is a poly-β1→4-glucosamine represented by the following chemical formula (I) (($C_6H_{11}NO_4)_n$, CAS Registry Number 9012-76-4).

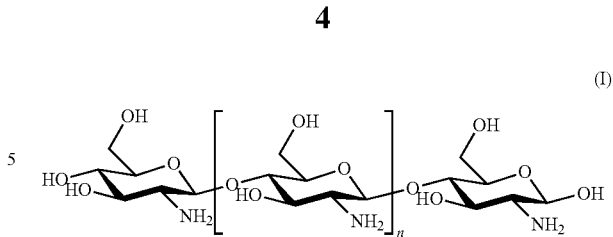

(I)

The chitosan is water soluble. The upper limit of the molecular weight of chitosan may be, for example, 30,000 Da or less, more preferably 25,000 Da or less, 20,000 Da or less, 18,000 Da or less, and 15,000 Da or less. The lower limit of the molecular weight of chitosan is not particularly limited, but may be, for example, 1,000 Da or more, preferably 5,000 Da or more, 10,000 Da or more, and 12,000 Da or more. The range of the molecular weight of the chitosan can be between the upper limit value and lower limit value of any of the above, for example, 1,000 Da to 30,000 Da, preferably 5,000 Da to 20,000 Da, and more preferably 10,000 Da to 15,000 Da. When focusing on antibacterial properties, chitosan having a larger molecular weight is more advantageous, and focusing on ease of production, chitosan having a smaller molecular weight has better solubility and stability, and chitosan having a lower molecular weight is more advantageous.

The cross-linking agent includes, for example, an amine-reactive cross-linking agent (such as alkoxyamine), a carbonyl-reactive cross-linking agent (such as hydrazine compound), a sulfhydryl-reactive cross-linking agent, and the like.

The mass ratio of lysozyme/chitosan is suitably, for example, 99/1 to 1/99, preferably 90/10 to 10/90, more preferably 80/20 to 20/80, further preferably 60/40 to 40/60, and particularly preferably 50/50.

A specific method for producing a complex of lysozyme and chitosan bound together includes the following, for example. First, lysozyme and chitosan having the above mass ratio are mixed and dissolved in water, and the total mass of lysozyme and chitosan in the obtained aqueous solution is adjusted to 5 to 30% by mass. The obtained aqueous solution is freeze-dried and pulverized. The resulting powder can be subjected to Maillard reaction, for example, for 2 to 20 days, more preferably for 7 to 14 days, under conditions of temperature of, for example, 50 to 80° C., preferably 55 to 65° C., and relative humidity of, for example, 50 to 80%, preferably 60 to 70%, to produce a complex of lysozyme and chitosan bound together of the present invention.

Whether or not the lysozyme-chitosan complex of the present embodiment has been formed can be confirmed by various known methods, and for example, by staining plates obtained by SDS (sodium dodecyl sulfate) or SDS-PAGE (sodium dodecyl sulfate-polyacrylamide) polyacrylamide electrophoresis, it is possible to confirm the formation of a macromolecular substance that is the protein-chitosan complex.

"Neutrophils" are a type of polymorphonuclear leukocyte found in the blood. Neutrophils migrate from blood vessels into tissues toward the site of inflammation, and feed on foreign substances at the site of inflammation. In addition, neutrophils have the ability to be activated to produce reactive oxygen species (such as hydrogen peroxide and hydroxyl radicals) and release the reactive oxygen species into the extracellular space, and release granule components such as proteolytic enzymes into the extracellular space. On the other hand, the production of excessive reactive oxygen species by activated neutrophils accumulated at the site of inflammation causes damaging effects (adverse effects) to cellular tissues other than the site of inflammation (Non-Patent Literatures 1 to 3). "Neutrophil-induced inflammation" is the manifestation of the damaging effects of such neutrophils. Therefore, the "neutrophil-induced inflammation" is different from inflammation caused by germs such as fungi and bacteria. The pharmaceutical composition of the present invention can significantly treat and/or prevent the "neutrophil-induced inflammation". Specific examples of the "neutrophil-induced inflammation" of the present invention include, for example, dermatitis such as allergic dermatitis, atopic dermatitis, seborrheic dermatitis, exfoliative dermatitis, stasis dermatitis, and contact dermatitis, psoriasis, eczema, and pyoderma.

Here, the term "treat" includes not only completely healing the inflammation which is the subject of the present invention, but also suppressing the inflammation and reducing its severity. The term "prevent" not only includes the case where there is no history of inflammation which is the subject of the present invention, but also includes prevention so that the inflammation which is the subject of the present invention does not recur after it has healed.

In addition to the above complex, the pharmaceutical composition of the present invention may optionally contain at least one additional active ingredient. The additional active ingredients include those that act as active ingredients by themselves, as well as those that do not act as active ingredients by themselves but exert their effects (auxiliary agents) when used in combination with the above complex, which is an active ingredient of the present invention. The additional active ingredients include, for example, terpene alcohols, fatty acids, and/or salts of the fatty acids. By adding these terpene alcohols, fatty acids, and/or salts of the fatty acids, additive effects and synergistic effects can be obtained in combination with the complex of the present invention. The terpene alcohols include, for example, terpinen-4-ol, hinokitiol, geraniol, menthol, and the like. The fatty acids include, for example, fatty acids having 8 to 12 carbon atoms, preferably decanoic acid (capric acid) or lauric acid. The salts of fatty acid salts include, for example, sodium salts, potassium salts, magnesium salts, calcium salts, and the like. In addition, essential oils obtained from lemongrass, spearmint, geranium, perilla, and the like, as well as glucosamine, which are known to be effective against neutrophil-induced inflammation, may be added as the additional active ingredients.

In addition to the above-mentioned complex, the pharmaceutical composition of the present invention may optionally contain at least one additional component. As the additional components, it is possible to add, for example, additives such as excipients, binders, emulsifiers, solvents, pressure-sensitive adhesives, disintegrants, thickeners, lubricants, colorants, fluidizers, and humectants.

The humectants include, for example, glycerin, butylene glycol, collagen, hyaluronic acid, and ceramide.

The binders include, for example, cellulose, methyl cellulose, hydroxyethyl cellulose, and sodium carboxymethyl cellulose.

The emulsifiers include, for example, lecithin, polyethylene glycol (PG), PG-hydrogenated castor oil, glycerin fatty acid ester, sorbitan fatty acid ester, ceteth, and the like.

The solvents include, for example, water, ethanol, 1-butanol, 2-butanol, 1-propanol, 2-propanol, 1-pentanol, and the like.

The lysozyme-chitosan complex of the present invention is suitably contained at, for example, 0.01 mg/ml to 50 mg/ml, preferably 0.01 mg/ml to 2 mg/ml, more preferably 0.05 mg/ml to 1 mg/ml, further preferably 0.1 mg/ml to 0.5 mg/ml, and particularly preferably 0.2 mg/ml to 0.4 mg/ml in the pharmaceutical composition of the present invention. In addition, the additional active ingredient is suitably contained at, for example, 0.001% by mass to 5.0% by mass, preferably 0.002% by mass to 0.2% by mass, more preferably 0.005% by mass to 0.1% by mass, further preferably 0.01% by mass to 0.05% by mass, and particularly preferably 0.02% by mass to 0.04% by mass in the pharmaceutical composition of the present invention. Furthermore, for the additional components, the appropriate content should be adjusted according to each component, but for example, the suitable content is 0.1% by mass to 90% by mass, preferably 1% by mass to 70% by mass, and more preferably 10% by mass to 50% by mass. Note that most of the pharmaceutical composition of the present invention can be a solvent such as water, and for example, the suitable content of the solvent in the pharmaceutical composition of the present invention is 95% by mass or more, preferably 98% by mass or more, more preferably 99% by mass or more, and further preferably 99.5% by mass or more. In addition, the fatty acids having 8 to 12 carbon atoms such as lauric acid and decanoic acid (capric acid) or salts of the fatty acids are suitably contained in the pharmaceutical composition of the present invention at, for example, 0.001% by mass to 5% by mass, preferably 0.005% by mass to 1% by mass, more preferably 0.01% by mass to 0.5% by mass, and particularly preferably 0.04% by mass to 0.2% by mass.

[Dose, Administration Form, and Administration Method]

For the pharmaceutical composition of the present invention, although it depends on the dosage form, target of administration, route of administration, target disease, symptoms, and the like, in the case of, for example, a spray agent sprayed on human skin, the daily dosage amount is, for example, 0.1 to 20 mg/kg body weight, preferably 0.2 to 10 mg/kg body weight, and further preferably 0.5 to 10 mg/kg body weight, and this amount is desirably administered once to several times (e.g., two, three, four, or eight times) a day. This dosage amount can be preferably applied not only to the spray agent but also to other formulations such as the cream described below.

The pharmaceutical composition of the present invention can be administered orally or parenterally, and no special technique is required for their formulation, and the pharmaceutical composition can be formulated using a general-purpose technique. Dosage forms include creams, ointments, cataplasms, liquids, spray agents, gels, injections, tablets, suppositories, capsules, granules, powders, eye drops, eye ointments, and the like, and creams, ointments, cataplasms, liquids, and spray agents are particularly preferable.

The administration method for the pharmaceutical composition of the present invention can be appropriately selected according to the above-mentioned administration forms. The administration method may be a known administration method, and for example, in the case of creams, the pharmaceutical composition of the present invention may be applied to an inflamed site at the above dosage amount.

<Treatment Method>

The present invention may also include a method for by suppressing or preventing neutrophil-induced inflammation by administering to a subject a pharmaceutical composition containing a complex of lysozyme and chitosan bound together.

Here, the "subject" includes not only humans but also mammals such as cats, dogs, monkeys, cows, and horses.

Definitions of lysozyme, chitosan, and the like, additional active ingredients and additional components, dosage amount, administration form, administration method, and the like are as described above.

<Use>

The present invention may also include the use of a complex of lysozyme and chitosan bound together in the production of a pharmaceutical composition for treating or preventing neutrophil-induced inflammation.

In the production of a pharmaceutical composition for treating or preventing neutrophil-induced inflammation, the complex of lysozyme and chitosan bound together is mixed with the components of the pharmaceutical composition other than the complex to obtain the pharmaceutical composition. As the mixing method, a known method can be used, and for example, in the case of a liquid, a complex of lysozyme and chitosan bound together and any of the above additional components are added to a solvent such as water, mixed, and if necessary, an emulsifier is added and mixed to form a dispersant or emulsion, and the liquid is prepared.

EXAMPLE

[Sample Preparation]
Neutrophil Suspension

Neutrophils were collected from blood. Specifically, neutrophils were isolated from whole blood collected from healthy humans or dogs using Polymorphprep (Cosmo Bio). The separated neutrophil samples were centrifuged at 2000 rpm for about 40 minutes, then the supernatant was removed, and the residue was transferred to RPMI (SIGMA) medium supplemented with 10-mass % fetal bovine serum (Tissue Culture Biologicals, USA) and diluted to obtain a cell count of $4 \times 10^6$ cells/ml, preparing human and canine neutrophil suspensions, respectively.

Activation Standard Solution

*E. coli*-derived lipopolysaccharide (SIGMA Lot 12K4083), an activating reagent for neutrophils, was diluted using RPMI (SIGMA) medium previously supplemented with 10-mass % fetal bovine serum (Tissue Culture Biologicals, USA) to obtain an activation standard solution in which the mass of *E. coli*-derived lipopolysaccharide was 4 µg/ml relative to the volume of the resulting activation standard solution.

Pharmaceutical Composition Sample of Present Invention

A commercially available LYZOX (registered trademark, manufactured by Wako Filter Technology Co., Ltd.) was used as a complex of lysozyme and chitosan bound together (lysozyme-chitosan complex). Commercially available LYZOX (registered trademark) is a powder containing chicken-derived lysozyme and 14,000 Da water-soluble chitosan in a 1:1 mass ratio. Specifically, the above lysozyme and water-soluble chitosan were mixed and dissolved in water and then lyophilized to form a powder, and then a Maillard reaction was carried out under conditions of temperature, humidity, and days sufficient for the Maillard reaction to be fully completed to obtain the lysozyme-chitosan complex (LYZOX (registered trademark)) used in the present invention.

[Evaluation of Anti-Inflammatory Effect]

The anti-inflammatory effect on neutrophil-induced inflammation can be grasped from the amount of neutrophil that adhere to the site of inflammation. Specifically, if the amount of neutrophil adhering to the site of inflammation is reduced after the application of the pharmaceutical composition of the present invention, the pharmaceutical composition of the present invention has the effect of suppressing neutrophil adhesion. If the amount of neutrophil adhering to the site of inflammation is reduced, the amount of reactive oxygen species produced in excess due to the neutrophils is reduced, thereby suppressing the inflammatory reactions caused by the reactive oxygen species. It is well known that there is a substantially linear correlation between neutrophil adhesion and the anti-inflammatory effect on neutrophil-induced inflammation (for example, Naoshi Yakuwa, et. al. "A Novel Neutrophil Adherent Test Effectively Reflects the Activated State of Neutrophils", Microbiol. Immunol. 1989; Vol. 33(10), see pages 843-852).

The neutrophil adhesion rate was determined as follows. The value obtained by quantifying the activated neutrophils adhered to the wells in the control without containing lysozyme-chitosan complex or decanoic acid was set as 100%, and compared with the value obtained by quantifying the activated neutrophils adhered to the wells in the same way for the test substances in each Example and Comparative Example.

Neutrophil Adhesion Rate (%)=[Quantitative Value of Adhesive Activated Neutrophils in Each Example and Comparative Example]/[Quantitative Value of Adhesive Activated Neutrophils in Control]×100

The experimental method and quantification method of each specific Example and Comparative Example are as shown below.

Example 1

In the present invention, the ability to suppress the neutrophil adhesive reaction was evaluated by the following procedure. Specifically, LYZOX (registered trademark) as a lysozyme-chitosan complex was diluted with RPMI (SIGMA) medium supplemented with 10-mass % fetal bovine serum (Tissue Culture Biologicals, USA) to obtain a test substance. To the 96-well plate well, 50 µl of the test substance, 50 µl of the activation standard solution, and 100 µl of the human neutrophil suspension were added. After 1 hour of incubation at 37° C. in an atmosphere of 5% $CO_2$, the supernatant containing neutrophils that had not adhered to the 96-well plate well (non-adherent cells) was removed, and activated neutrophils that had tightly adhered to the bottom of the wells were washed with saline and dried. After drying for 16 hours, 200 µl of 1% crystal violet (Merk) was added to each well, which was allowed to stand for 15 minutes, and the adherent neutrophils (adherent cells) in each well were stained with (crystal violet), and 100 µl of 1% SDS (Sodium dodecyl sulfate) was added to each well and mixed sufficiently, and the transmittance (absorbance, or $OD_{620}$) was measured when light of 620 nm wavelength was applied using a microplate reader to quantify the activated neutrophils adherent to each well.

Figure 2:
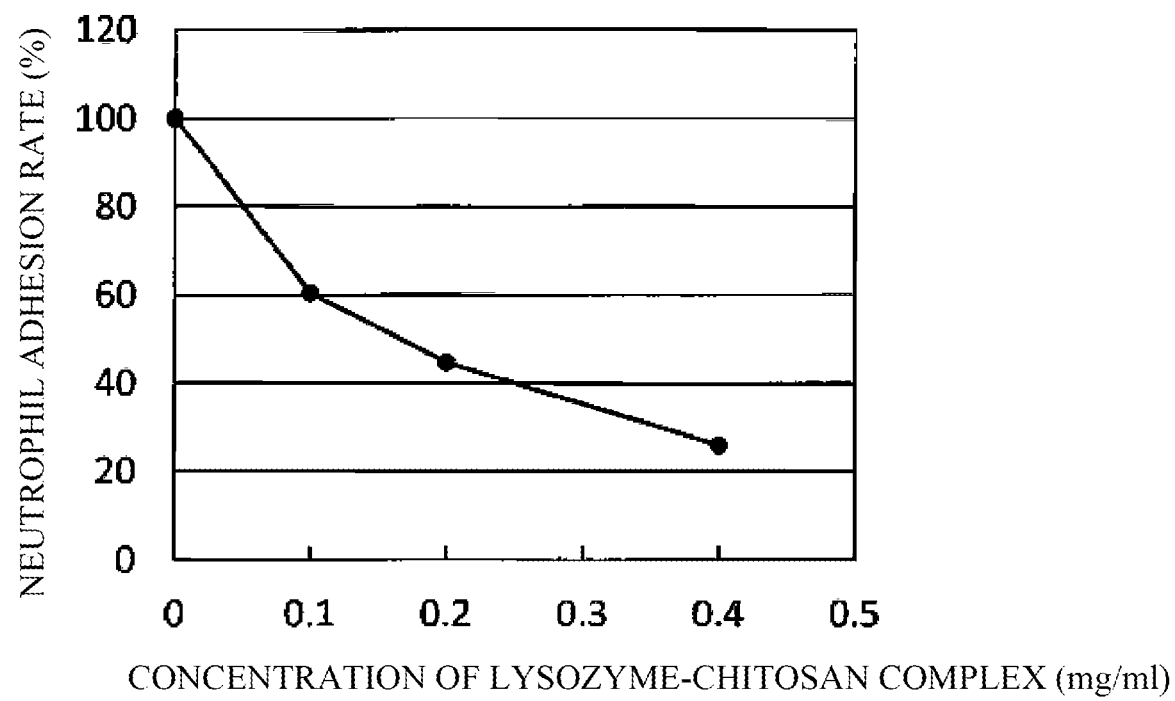
FIG. 2A is a graph showing the relationship between the concentration of the lysozyme-chitosan complex and the neutrophil adhesion rate (%).
FIG. 2B is a graph showing the relationship between the concentration of decanoic acid and the neutrophil adhesion rate (%).
Figure 2:
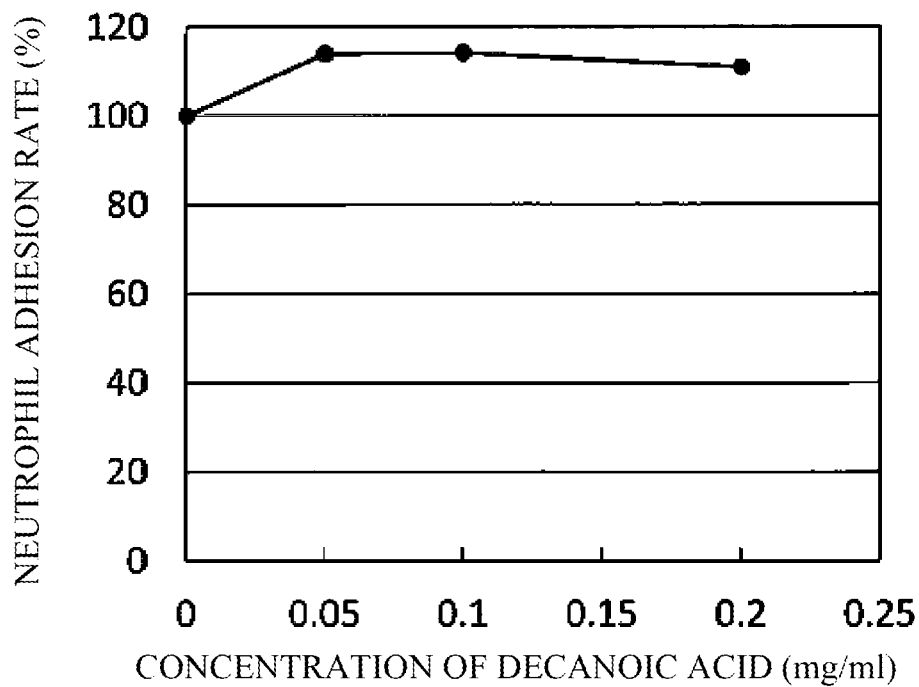

FIG. 2A shows the relationship between the concentration of LYZOX (registered trademark) (lysozyme-chitosan complex) and the neutrophil adhesion rate (%) when tested with the LYZOX (registered trademark) as described above.

Comparative Example 1

The test was repeated in the same manner as in Example 1 except that decanoic acid was used instead of LYZOX (registered trademark) to quantify the activated neutrophils adhering to the 96-well plate well. FIG. 2B shows the relationship between the concentration of decanoic acid and the neutrophil adhesion rate (%) when tested using decanoic acid in this way.

As can be seen from the contrast between FIG. 2A and FIG. 2B, as the concentration of LYZOX (registered trademark) (lysozyme-chitosan complex) increases, the neutrophil adhesion rate (%) decreases, indicating that LYZOX (registered trademark) has an anti-inflammatory effect on neutrophil-induced inflammation. Meanwhile, when decanoic acid was used, the neutrophil adhesion rate (%) did not decrease as the concentration of decanoic acid increased, indicating that decanoic acid cannot be expected to have an anti-inflammatory effect on neutrophil-induced inflammation.

Example 2

The same test as in Example 1 was repeated except that a canine neutrophil suspension was used as the neutrophil suspension and various test substances were used as the test substances to quantify the activated neutrophils adhering to the 96-well plate well. At the same time, neutrophils adhering to the 96-well plate well (adherent cells) were stained with crystal violet and observed under a microscope. The test substances used are as follows.
- (a): Control (free of lysozyme-chitosan complex and decanoic acid)
- (b): A mixture of 0.2 mg/ml lysozyme-chitosan complex (0.02% by mass based on the total mass of the test substance) and 0.4 mg/ml decanoic acid (0.04% by mass based on the total mass of the test substance).
- (c): 0.2 mg/ml lysozyme-chitosan complex (0.02% by mass based on the total mass of the test substance)
- (d): 0.4 mg/ml decanoic acid (0.04% by mass based on the total mass of the test substance)

FIGS. 3A to 3D show photomicrographs of neutrophils adhering to the 96-well plate well, stained with crystal violet, in the case of using the above test substances (a) to (d), respectively. As a microscope, an inverted system microscope MODEL IMT-2 manufactured by Olympus was used, and the observation magnification was set to 40 times.

In addition, FIG. 4 shows the neutrophil adhesion rate (%) in the case of using the above test substances (a) to (d).

Figure 3A:
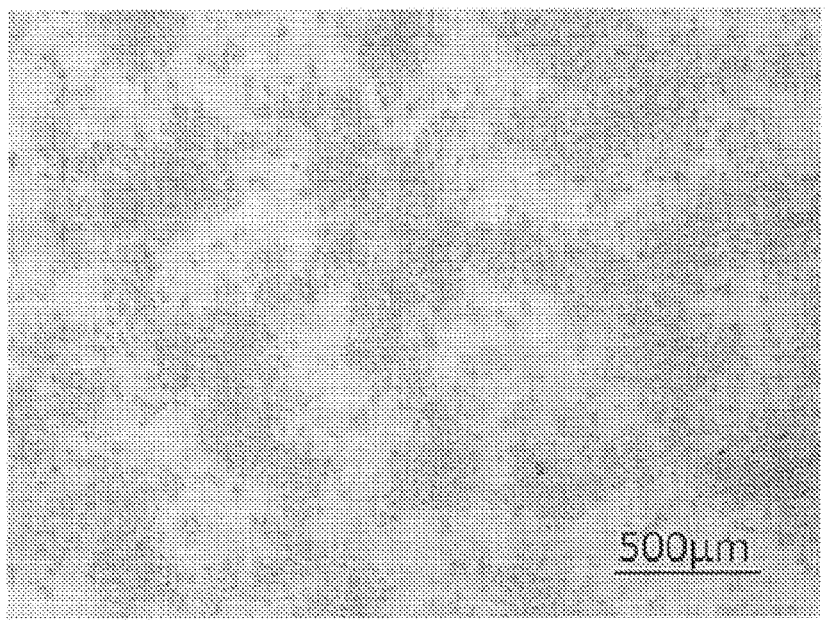
FIG. 3A is a photomicrograph showing control neutrophils stained with crystal violet, free of lysozyme-chitosan complex and decanoic acid.
Figure 3B:
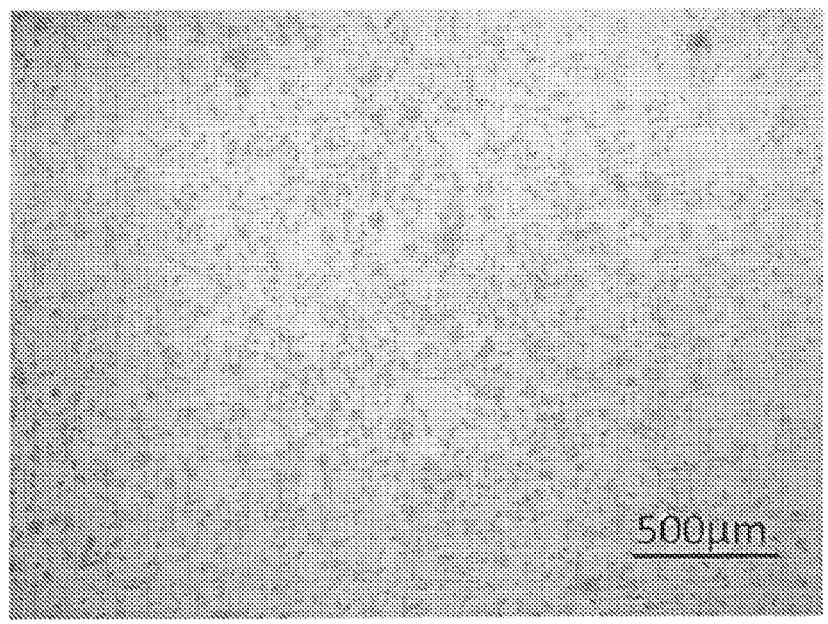
FIG. 3B is a photomicrograph showing neutrophils stained with crystal violet in the case of using a mixture of 0.2 mg/ml lysozyme-chitosan complex and 0.4 mg/ml decanoic acid.
Figure 3C:
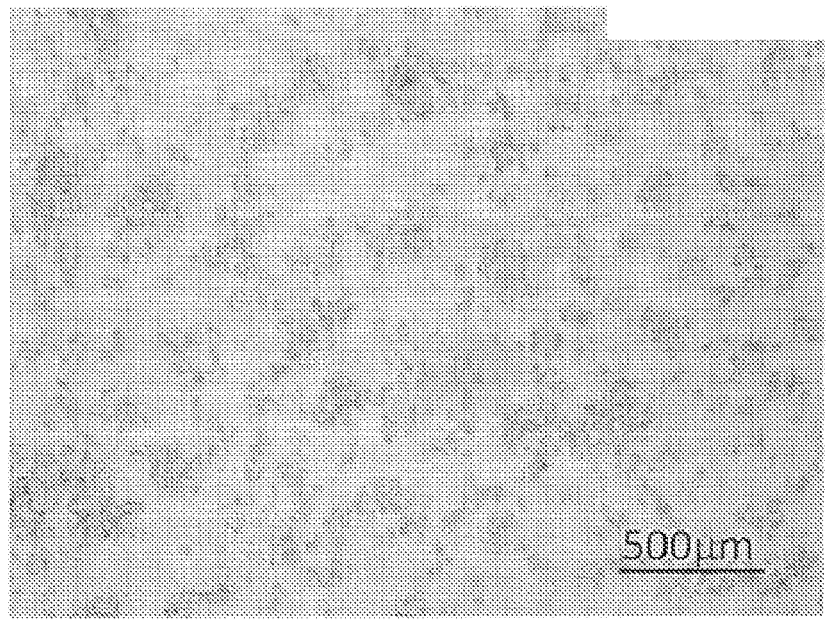
FIG. 3C is a photomicrograph showing neutrophils stained with crystal violet in the case of using 0.2 mg/ml lysozyme-chitosan complex.
Figure 3D:
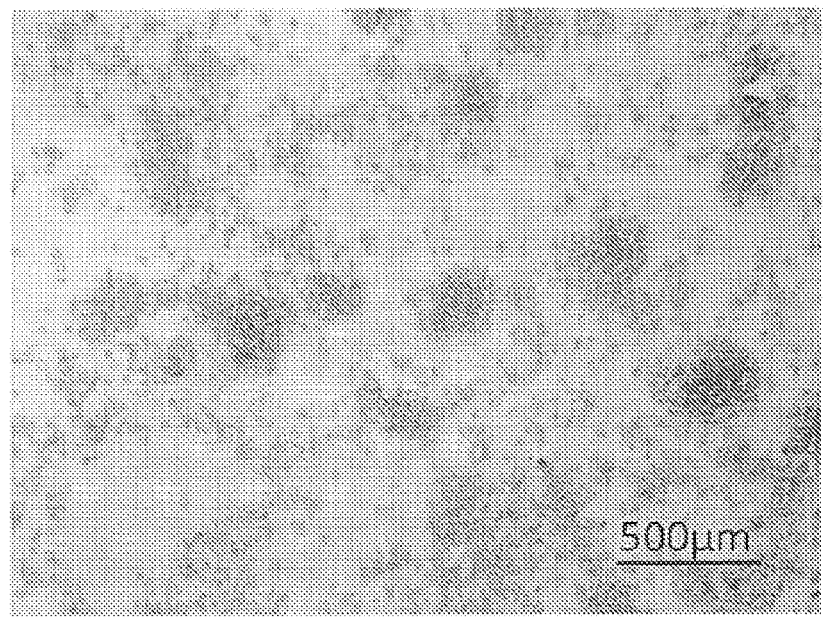
FIG. 3D is a photomicrograph showing neutrophils stained with crystal violet in the case of using 0.4 mg/ml decanoic acid.

As shown in FIG. 3A to FIG. 3D, it can be seen that the neutrophils stained with crystal violet are widely distributed in FIG. 3A and FIG. 3D, while the distribution of the neutrophils stained with crystal violet is suppressed in FIG. 3B and FIG. 3C. In addition, as shown in FIG. 4, it can be seen that (b) lysozyme-chitosan complex+decanoic acid and (c) lysozyme-chitosan complex significantly suppress the neutrophil adhesion rate (%) compared to (a) control and (d) decanoic acid alone.

What is claimed is:

1. A pharmaceutical composition for treating or preventing neutrophil-induced inflammation, comprising: decanoic acid and a complex of lysozyme and chitosan bound together, wherein the complex is contained at 0.01 mg/ml to 50 mg/ml in the pharmaceutical composition.

2. The pharmaceutical composition according to claim 1, wherein the chitosan is a water-soluble chitosan having a molecular weight of 1000 Da to 30,000 Da.

3. The pharmaceutical composition according to claim 1, wherein the complex is contained at 0.001% by mass to 5.0% by mass in the pharmaceutical composition.

4. The pharmaceutical composition according to claim 1, further comprising a terpene alcohol.

5. The pharmaceutical composition according to claim 1, further comprising a terpene alcohol, wherein the terpene alcohol is terpinen-4-ol, hinokitiol, or geraniol.

6. The pharmaceutical composition according to claim 1, wherein the neutrophil-induced inflammation is dermatitis or pyoderma.

7. A method for treating or preventing neutrophil-induced inflammation, comprising a step of administering to a subject a pharmaceutical composition containing decanoic acid and a complex of lysozyme and chitosan bound together so as to suppress or prevent neutrophil-induced inflammation, wherein the complex is contained at 0.01 mg/ml to 50 mg/ml in the pharmaceutical composition.

8. The method according to claim 7, wherein the chitosan is a water-soluble chitosan having a molecular weight of 1000 Da to 30,000 Da.

9. The method according to claim 7, wherein the complex is contained at 0.001% by mass to 5.0% by mass in the pharmaceutical composition.

10. The method according to claim 7, wherein the pharmaceutical composition further comprises a terpene alcohol.

11. The method according to claim 7, wherein the pharmaceutical composition further comprises a terpene alcohol, wherein the terpene alcohol is terpinen-4-ol, hinokitiol, or geraniol.

12. The method according to claim 7, wherein the neutrophil-induced inflammation is dermatitis or pyoderma.

* * * * *